United States Patent
Idestam-Almquist

(10) Patent No.: US 12,216,831 B2
(45) Date of Patent: Feb. 4, 2025

(54) COMMUNICATIONS SYSTEM AND A METHOD FOR COMMUNICATING INFORMATION

(71) Applicant: Peter Idestam-Almquist, Solna (SE)

(72) Inventor: Peter Idestam-Almquist, Solna (SE)

( * ) Notice: Subject to any disclaimer, the term of this patent is extended or adjusted under 35 U.S.C. 154(b) by 0 days.

(21) Appl. No.: 18/054,672

(22) Filed: Nov. 11, 2022

(65) Prior Publication Data

US 2023/0152901 A1    May 18, 2023

(30) Foreign Application Priority Data

Nov. 17, 2021  (SE) .................................... 2151399-9

(51) Int. Cl.
    *G06F 3/01*    (2006.01)
(52) U.S. Cl.
    CPC .................................... *G06F 3/017* (2013.01)
(58) Field of Classification Search
    None
    See application file for complete search history.

(56) References Cited

U.S. PATENT DOCUMENTS

| | | | | |
|---|---|---|---|---|
| 8,344,862 | B1 * | 1/2013 | Donham | H04M 1/7243 |
| | | | | 455/66.1 |
| 9,754,464 | B1 * | 9/2017 | Sinkov | G06F 1/163 |
| 10,765,908 | B1 * | 9/2020 | Uehara | A63B 21/4001 |
| 2008/0254747 | A1 * | 10/2008 | Fu | H04B 1/406 |
| | | | | 455/66.1 |
| 2009/0326406 | A1 * | 12/2009 | Tan | G06F 3/017 |
| | | | | 341/20 |
| 2014/0240103 | A1 * | 8/2014 | Lake | G06F 1/163 |
| | | | | 340/12.5 |
| 2016/0019817 | A1 * | 1/2016 | Deokar | G09B 21/02 |
| | | | | 340/4.12 |
| 2018/0153430 | A1 * | 6/2018 | Ang | A61B 5/24 |

(Continued)

FOREIGN PATENT DOCUMENTS

WO    2020/109455 A1    6/2020

OTHER PUBLICATIONS

Swedish Office Action dated Jul. 8, 2022 for corresponding Swedish Application No. 2151399-9 and English translation.

(Continued)

*Primary Examiner* — Parul H Gupta
(74) *Attorney, Agent, or Firm* — Chrisman Gallo Tochtrop LLC

(57) ABSTRACT

A wearable sensor configuration that is configured to operate in a communications system and method is provided. The wearable sensor configuration includes at least one sensor unit being arranged to detect signals from activity of muscles of a user. Thus, the wearable sensor configuration includes at least one sensor unit that is arranged to detect signals from muscle activity of a user of the communications system, such as for example, signals generated by movements and/or muscle activity of a user of the communications system. The wearable sensor configuration can also include a first electronic arrangement that is arranged to determine Internal Digital Information based on detected signals by means of a first mapping function. The Internal Digital Information can also be transmitted to a second electronic arrangement. The Internal Digital Information may be transmitted wirelessly.

5 Claims, 5 Drawing Sheets

(56) References Cited

U.S. PATENT DOCUMENTS

| | | | | |
|---|---|---|---|---|
| 2018/0287649 A1* | 10/2018 | Kim | .................... | H04W 76/50 |
| 2019/0142349 A1* | 5/2019 | Schorey | .................. | A61B 5/11 |
| | | | | 600/546 |
| 2021/0064132 A1* | 3/2021 | Rubin | .................. | G06F 3/0237 |
| 2023/0283356 A1* | 9/2023 | Li | ............................ | G01S 7/03 |

OTHER PUBLICATIONS

Swedish Office Action dated Oct. 12, 2023 for corresponding Swedish Application No. 2151399-9.
Extended European Search Report dated Mar. 17, 2023 for corresponding European Patent Application No. 22206726.6.

* cited by examiner

COMMUNICATIONS SYSTEM AND A METHOD FOR COMMUNICATING INFORMATION

CROSS-REFERENCE TO RELATED APPLICATIONS

This application claims benefit of Swedish Application No. 2151399-9 filed on Nov. 17, 2021, the entire contents of which are incorporated herein by reference.

TECHNICAL FIELD

The present invention relates to a method for communicating information within a communications system. It also relates to a communications system. The invention also relates to a computer program product comprising program code for a computer for implementing a method according to the invention.

BACKGROUND ART

In the HCI (Human Computer Interaction) area, muscle activity sensors (EMG electromyography) have been used for gesture recognition, not for input of text-based information. In the BCI (Brain Computer Interfaces) area, muscle activity sensors have been used for controlling external devices such as prostheses. However, brain activity sensors (EEG—electroencephalography) have been used for text-based input, but this technology is far from being ready for public use.

Existing input devices for text-based information (verbal information) to computer devices requires either some kind of physical buttons (keyboards), touchscreen, or microphone (together with speech recognition software). All such input devices are from the user perspective external devices that the user needs to aim the input at, whether it is a keyboard, touchscreen or microphone.

OBJECTS OF THE INVENTION

An object of the present disclosure is to provide a communications system, which seeks to mitigate, alleviate, or eliminate one or more of the above-identified deficiencies and disadvantages in the art, singly or in any combination.

An object of the present invention is to propose a novel and advantageous method for communicating information in a communications system.

Another object of the present invention is to propose a novel and advantageous method providing a reliable, simple-to-use and accurate communication of information within a communications system.

Yet another object of the invention is to propose a method, a communications system and a computer program achieving a user-friendly communication of information within a communications system, where the user is experiencing that he/she is communicating through his/her body.

Yet another object of the invention is to propose an alternative method for communication of information within a communications system, an alternative communications system and an alternative computer program for communication of information within a communications system.

SUMMARY

These and other objects, apparent from the following description, are achieved by a communications system, a method for communicating information from a sensor configuration in a communications system, a computer program product and a computer readable medium.

Specifically, objects of the invention are achieved by a wearable sensor configuration arranged to operate in a communications system. The wearable sensor configuration comprises at least one sensor unit being arranged to detect signals from activity of muscles of a user. Thus, the wearable sensor configuration comprises at least one sensor unit that is arranged to detect signals from muscle activity of a user of the communications system, i.e. signals generated by movements/muscle activity of a user of the communications system. The wearable sensor configuration further comprises a first electronic arrangement being arranged to determine Internal Digital Information on the basis of the detected signals by means of a first mapping function. The wearable sensor configuration further comprises means being arranged to transmit the Internal Digital Information to a second electronic arrangement. The Internal Digital Information may be transmitted wirelessly.

It is hereby advantageous to use a binary signal detection (just to differentiate between signal on and signal off, not any intermediate values) and translate these binary signals to text. This drastically simplifies the signal detection and increases the information quality, which makes this technique practically useful. However, it requires the user to learn some encoding scheme such as Morse code. The binary signal detection does not have to be to detect the difference between tensed muscles and relaxed muscles, but could also for example be to detect the difference between movement and stillness of e.g. a finger or an arm of the user by using an accelerometer.

According to an example of the disclosure, the sensor unit is an electromyography sensor, and the detected signals are electro potential signals.

According to an example of the disclosure, the sensor unit is an accelerometer sensor, and the detected signals are g-force signals.

The first mapping function may be set-up by predetermined rules and/or by choice of a user.

According to an aspect of the present disclosure there is proposed a communications system comprising the wearable sensor configuration, the communications system may comprise:

the second electronic arrangement, which is arranged to receive the Internal Digital Information from the wearable sensor configuration, and wherein the second electronic arrangement may be arranged to determine Textual Information on the basis of the Internal Digital Information by means of a second mapping function. The communications system may further comprise means being arranged to determine Intermediate Information on the basis of the Internal Digital Information. The communications system may thus further comprise the second electronic arrangement being arranged to determine Intermediate Information on the basis of the Internal Digital Information The communications system may further comprise means being arranged to determine Textual Information on the basis of the Intermediate Information and/or the Internal Digital Information by means of the second mapping function.

The communications system may thus further comprise the second electronic arrangement being arranged to determine Textual Information on the basis of the Intermediate Information and/or the Internal Digital Information by means of the second mapping function.

The second mapping function may be set-up by predetermined rules and/or by choice of a user.

The second electronic arrangement may be arranged to transmit the Textual Information to a third electronic arrangement.

The second electronic arrangement may be arranged to include the Textual Information in a message according to a certain message format of a messaging application installed on the second electronic arrangement and the third electronic arrangement. The message format may be SMS, E-mail, etc.

According to an aspect of the present disclosure there is provided a method for communicating information from a wearable sensor configuration comprising a sensor unit and a first electronic arrangement, wherein the wearable sensor configuration is arranged to operate in a communications system, the method comprising:

- detecting signals from activity of muscles of a user, i.e. signals generated by muscle activity of a user of the communications system;
- determining Internal Digital Information on the basis of the detected signals by means of a first mapping function in the first electronic arrangement;
- communicating the Internal Digital Information to a second electronic device from the wearable sensor configuration; and
- determining Textual Information on the basis of the Internal Digital Information by means of a second mapping function in the second electronic arrangement.

The method may further comprise the steps of:
- determining Intermediate Information on the basis of Internal Digital Information; and
- determining Textual Information on the basis of the Intermediate Information and/or the Internal Digital Information by means of the second mapping function.

The method may further comprise the steps of:
- setting-up the first mapping function by predetermined rules and/or by choice of a user; and/or
- setting-up the second mapping function by predetermined rules and/or by choice of a user.

An aspect of the present disclosure relates to a wearable sensor configuration (also denoted wearable device), for example a wristband, with muscle activity sensors to enable text-based input to computer devices without any keyboard, touchscreen, or microphone. The user can use its own body as an input device, for example by moving a finger.

The wearable device is arranged to, via wire or wirelessly, for example a Bluetooth Low Energy (BLE) connection, transmit the internal digital information to the second electronic arrangement, for example a smartphone. The second electronic arrangement may be in possession of a first user of the communications system.

The second mapping function on the second electronic arrangement is arranged to convert the Internal Digital Information into Textual Information. This could for example be done in a two-step process where in the first step the Internal Digital Information is converted to an Intermediate Information in Morse code. Hereby portions of the signal is either interpreted as a dot or a dash in Morse code. Hereby portions of the signal is interpreted as an interelement gap within a character, a gap between characters or a gap between words in Morse code. The second step of the conversion uses the international Morse code standard to translate the intermediate information in Morse code into Textual Information. Machine learning techniques may be used to adopt the second mapping function to the Internal Digital Information generated by a specific user. The textual information can be transmitted via wire or wirelessly to a third electronic arrangement. The third electronic arrangement may be in possession of a second user of the communications system.

According to an aspect of the invention there is provided a computer program product comprising instructions that, when the program is executed by a computer, cause the computer to carry out any one of the steps of the method depicted herein.

According to an aspect of the invention there is provided a computer-readable storage medium comprising instructions that, when executed by a computer, cause the computer to carry out any one of the steps of the method depicted herein.

The term "link" refers herein to a communication link, which may be a physical connection such as a multicore cable, an opto-electronic communication line, or a non-physical connection such as a wireless connection, e.g. a radio link or microwave link.

The term "electronic arrangement" is according to one embodiment herein defined as an arrangement comprising only one electronic arrangement or a number of connected electronic arrangements. Said one electronic arrangement or said number of connected electronic arrangements may be arranged to perform the steps according to the method depicted herein.

The terminology used herein is for the purpose of describing particular aspects of the disclosure only and is not intended to limit the disclosure. As used herein, the singular forms "a", "an" and "the" are intended to include the plural forms as well, unless the context clearly indicates otherwise.

In some implementations and according to some aspects of the disclosure, the functions or steps noted in the blocks can occur out of the order noted in the operational illustrations. For example, two blocks shown in succession can in fact be executed substantially concurrently or the blocks can sometimes be executed in the reverse order, depending upon the functionality/acts involved. Also, the functions or steps noted in the blocks can according to some aspects of the disclosure be executed continuously in a loop.

It should be emphasized that the term "comprises/comprising" when used in this specification is taken to specify the presence of stated features, steps, or components, but does not preclude the presence or addition of one or more other features, steps, components, or groups thereof.

It should further be noted that any reference signs do not limit the scope of the claims, that the example embodiments may be implemented at least in part by means of both hardware and software, and that several "arrangements", "means", "units" or "devices" may be represented by the same item of hardware.

Further objects, advantages and novel features of the present invention will become apparent to one skilled in the art from the following details, and also by putting the invention into practice. Whereas the invention is described below, it should be noted that it is not confined to the specific details described. One skilled in the art having access to the teachings herein will recognise further applications, modifications and incorporations in other fields, which are within the scope of the invention.

BRIEF DESCRIPTION OF THE DRAWINGS

For fuller understanding of embodiments of the present invention and its further objects and advantages, the detailed description set out below should be read in conjunction with the accompanying drawings, in which the same reference notations denote similar items in the various diagrams, and in which.

DETAILED DESCRIPTION

Figure 1:
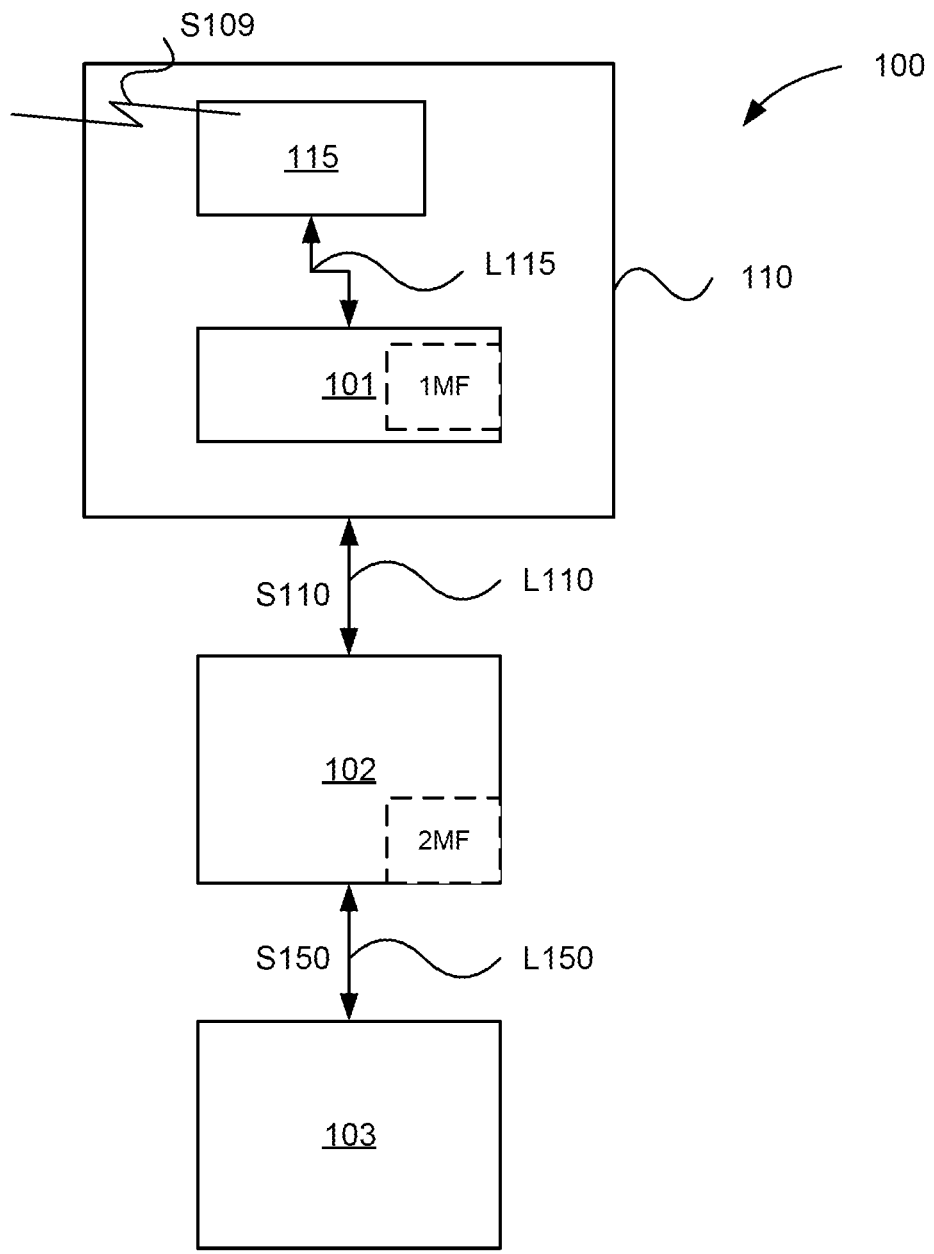
FIG. 1 schematically illustrates a communications system according to an embodiment of the present disclosure.

FIG. 1 schematically illustrates a communications system 100 according to an aspect of the present disclosure.

The communications system 100 comprises a sensor configuration 110. The sensor configuration 110 is according to an example a wearable device. The sensor configuration 110 is arranged to be worn by a user of the communications system 100. According to this example the sensor configuration 110 is designed as a wristband. Alternatively, the sensor configuration may be designed as, or incorporated in, a wristwatch, bracelet, necklace, anklet, headband or any other wearable device placed on a user so that muscle activity is possible to detect according to the proposed method. The sensor configuration 110 may be any suitable sensor configuration being arranged to detect muscle activity of the user of the communications system 100. The sensor configuration 110 may according to different embodiments be applied to various body parts of the user, e.g. a finger, foot or ankle. According to one example, the sensor configuration 110 may be provided in glasses, mask, visor or a head up display worn by the user. Hereby the sensor configuration 110 is arranged to detect muscle activity of the eyes of the user, such as muscle activity related to eye blinking.

The sensor configuration 110 is arranged with a sensor unit 115. The sensor unit 115 is arranged to detect muscle activity of the user of the communications system 100. According to one example, the sensor unit 110 comprises an electromyography (EMG) sensor that is arranged to detect signals S109, such as electrical signals, from muscle activity of the user of the communications system 100.

According to one example, the sensor configuration 110 may comprise one or more accelerometers being arranged to detect movements of the user, such as e.g. finger movements, arm movements, head movements, foot movements and/or leg movements.

According to an aspect of the disclosure, the proposed method and communications system is adapted to perform the proposed communication based on data determined by the one or more accelerometers.

The sensor configuration 110 comprises a first electronic arrangement 101. The first electronic arrangement 101 is arranged for communication with the sensor unit 115 via a link L115. The sensor unit 115 is arranged to detect the electric signals S109 and transmit the detected signals S109 to the first electronic arrangement 101 via the link L115. Examples of the detected signals S109 are further illustrated with reference to FIG. 3a-c.

The first electronic arrangement 101 is arranged to convert the received signals S109 to internal digital information IDI. The first electronic arrangement 101 is according to one example arranged to convert the received signals S109 to internal digital information IDI by means of a first mapping function 1MF. The first mapping function 1MF may be stored in a memory of the first electronic arrangement 101. The first mapping function 1MF may be denoted first mapping table.

According to one example the first mapping function 1MF is set up by predetermined rules.

According to one example, the first mapping function 1MF is set up by a user of the communications system 100.

According to one example machine learning techniques may be used to adopt the first mapping function 1MF to the detected signals S109 generated by a specific user.

The internal digital information IDI is according to one example a sequence of pairs (X,T), where X is either 1 (signal goes above threshold) or 0 (signal goes below threshold). In case the detected signal S109 is exceeding a predetermined threshold value Th it is determined that X is set to the value 1. In case the detected signal S109 is lower than a predetermined threshold value Th it is determined that X is set to the value 0. Herein T is a timestamp in milliseconds. According to one example, a pair (X,T) is created whenever a moving average of the amplitude of the detected signal S109 is above or below the predetermined threshold value Th for a certain amount of time. This is further illustrated with reference to e.g. FIGS. 3a-c.

The first electronic arrangement 101 is arranged for communication with a second electronic arrangement 102 via a link L110. The first electronic arrangement 101 is arranged to transmit signals S110 comprising the internal digital information IDI to the second electronic arrangement 102 via the link L110. The second electronic arrangement 102 may be a wireless communication device. The second electronic arrangement may be any kind of electronic arrangement, such as a mobile phone, smartphone, smartwatch, smart TV, tablet or laptop.

The second electronic arrangement 102 is according to one example arranged to convert the received signals S110 comprising the Internal Digital Information IDI to Intermediate Information II in Morse code. Hereby a sequence of pairs $(X_1, T_1), (X_2, T_2)- \ldots -(X_n, T_n)$, where "n" is a positive integer, is converted to Morse code comprising "dash" and "dot", as well as inter-element gap, inter-character gap or inter-word gap. Hereby a portion of the detected signal is either interpreted as a dot or a dash in Morse code. Hereby a portion of the detected signal may be interpreted as an inter-element gap within a character, a gap between characters or a gap between words in Morse code.

The second electronic arrangement 102 is arranged to convert the Intermediate Information II to Textual Information TI, such as e.g. alphanumerical characters, signs or symbols. The second electronic arrangement 102 is according to one example arranged to convert the Intermediate Information II to Textual Information TI by means of a second mapping function 2MF. The second mapping function 2MF may be stored in a memory of the second electronic arrangement 102. The second mapping function 2MF may be denoted second mapping table.

According to one example, the second mapping function 2MF is set up by predetermined rules.

According to one example, the second mapping function 2MF is set up by a user of the communications system 100. According to one example the International Morse code standard is used to translate the Intermediate Information II in Morse code into the textual information TI, however other Morse codes, or any other suitable code, may be used.

According to one example, machine-learning techniques may be used to continuously or intermittently adopt the second mapping function 2MF to the Internal Digital Information IDF generated by a specific user.

The second electronic arrangement 102 is arranged for communication with a third electronic arrangement 103 via a link L150. The second electronic arrangement 102 is arranged to transmit a signal S150 comprising the Textual Information TI to the third electronic arrangement 103 via the link L150. The third electronic arrangement 103 may be in possession of a second user of the communications system 100.

The textual information may be transmitted as an electronic message over a cellular network or an internet connection, as an SMS, e-mail or any kind of push notification.

Figure 2:
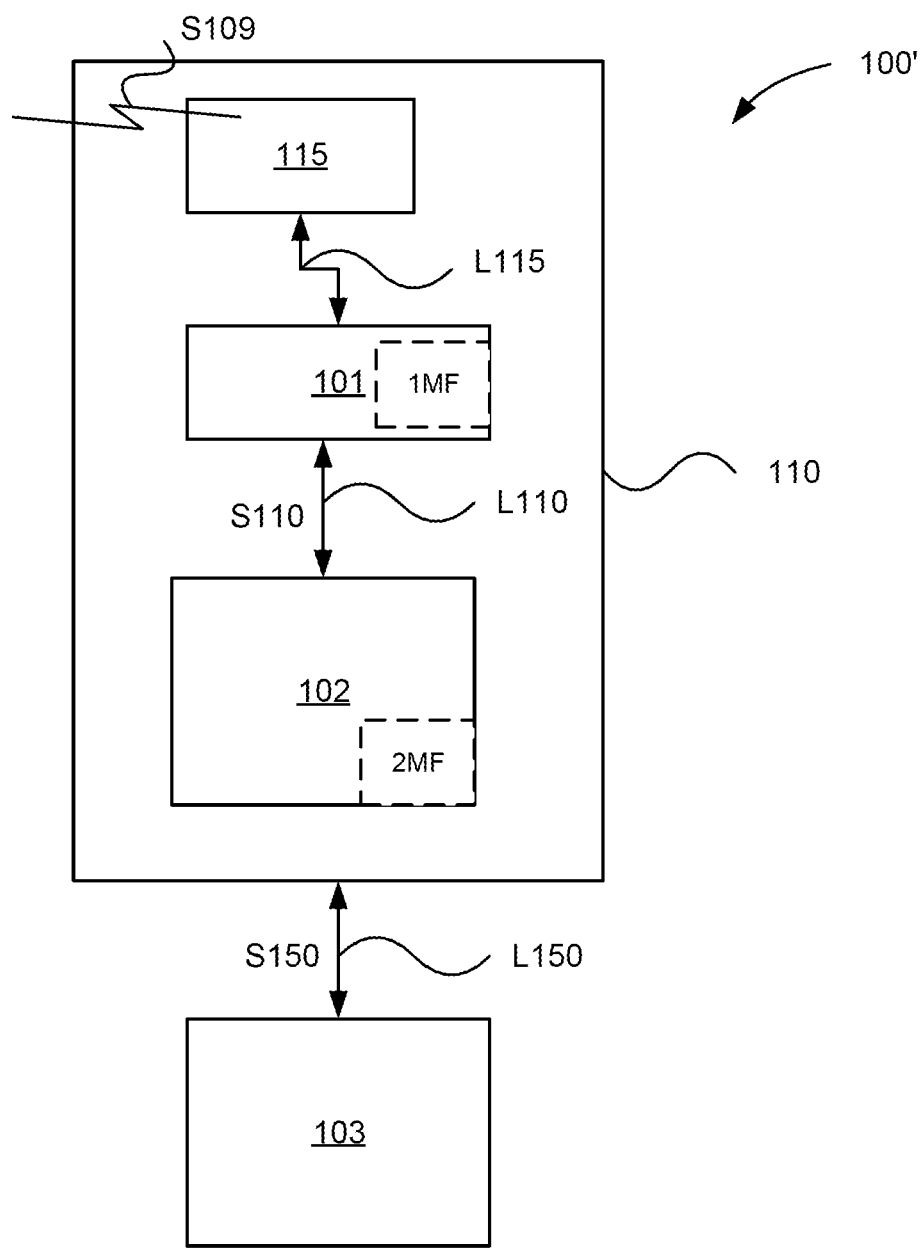
FIG. 2 schematically illustrates a communications system according to an embodiment of present disclosure.

FIG. 2 schematically illustrates another example of a communications system 100' according to an aspect of the present disclosure.

Herein the components of the communications system depicted with reference to FIG. 1 are denoted with corresponding reference numbers, however the alternative communications system 100' is configured in a different way. Herein the second electronic arrangement 102 is an integrated part of the sensor configuration 110.

According to an embodiment the second electronic arrangement 102 is arranged to transmit the signal S150 comprising the Textual Information TI to the third electronic arrangement 103 via the link L150. Hereby the Textual Information TI is transmitted directly from the sensor configuration 110 to the third electronic arrangement 103.

According to an embodiment, the sensor configuration 110 is arranged to transmit the signal S109 directly to the third electronic arrangement 103. Hereby the third electronic arrangement 103 is arranged to determine the Textual Information itself by means of the first mapping function 1MF and the second mapping function 2MF. According to this example, the first mapping function 1MF and the second mapping function 2MF are stored in a memory of the third electronic arrangement 103.

Figure 3A:
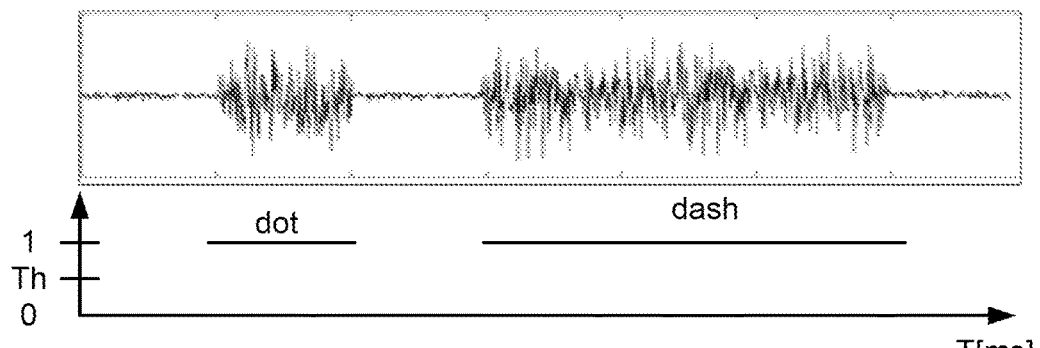
FIGS. 3a-c each schematically illustrates graphs presenting detected muscle activity signals according to examples of present disclosure.
Figure 3B:
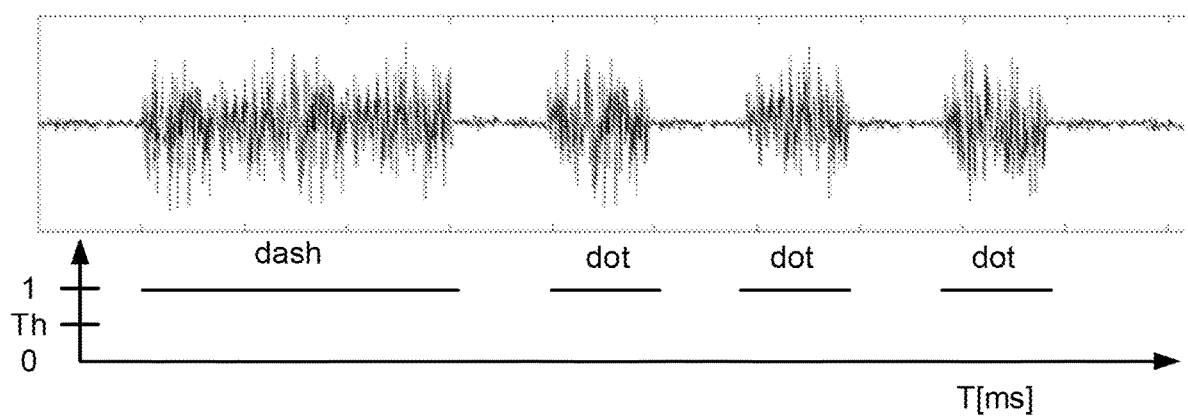
Figure 3C:
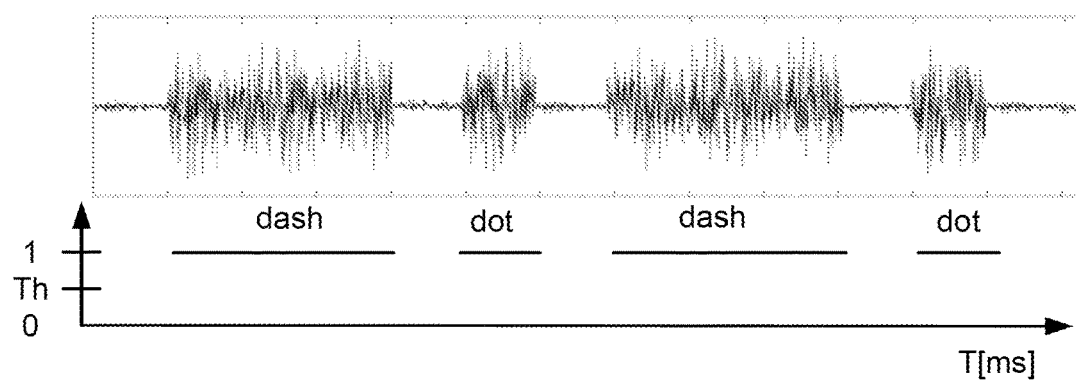

FIG. 3a schematically illustrates a first example of data conversion according to an embodiment of the disclosure. In an upper graph muscle activity data [micro Volt [μV]] is given as a function of time [ms]. The upper graph is an example of the signal S109, which has been detected by means of the sensor unit 115. In a lower graph a corresponding signal value (1 or 0) is given as a function of time [ms]. In case a moving absolute average value of the signal S109 is above a predetermined threshold value Th the function is given the value 1. In case the moving absolute average value of the signal S109 is below a predetermined threshold value Th the function is given the value 0. FIG. 3b and FIG. 3c are set out in a similar way.

According to this first example, the detected signal S109 is converted to Internal Digital Information, namely a number of pairs (X, T): (1,103), (0,199), (1,291), (0,585). Points of time are not indicated in the graphs. Herein the first pair of the internal digital data has a value 1 and a timestamp of 103 ms. The first pair represents the start of a "dot" in Morse code. Herein the second pair of the internal digital data has a value 0 and a timestamp of 199 ms. The second pair represents the start of an inter-element gap within a character in Morse code. Herein the third pair of the internal digital data has a value 1 and a timestamp of 291 ms. The third pair represents the start of a "dash" in Morse code. Herein the fourth pair of the internal digital data has a value 0 and a timestamp of 585 ms. The fourth pair represents the start of a gap between characters.

Intermediate Information II in Morse code according to this example is thus (dot, dash). In turn, corresponding textual information TI is the character "A". FIG. 3b schematically illustrates a second example of data conversion according to an embodiment of the disclosure.

According to this example IDI (based on the signal S109 illustrated in the upper graph) is: (1,108), (0,404), (1,489), (0,584), (1,681), (0,784), (1,870), (0,973).

Intermediate Information II in Morse code according to this example is thus (dash, dot, dot, dot). In turn, corresponding textual information TI is the character "B".

FIG. 3c schematically illustrates a third example of data conversion according to an embodiment of the disclosure.

According to this example, IDI (based on the signal S109 illustrated in the upper graph) is: (1,106), (0,402), (1,491), (0,587), (1,683), (0,1010), (1,1093), (0,1195).

Intermediate Information II in Morse code according to this example is thus (dash, dot, dash, dot). In turn, corresponding textual information TI is the character "C".

Figure 4:
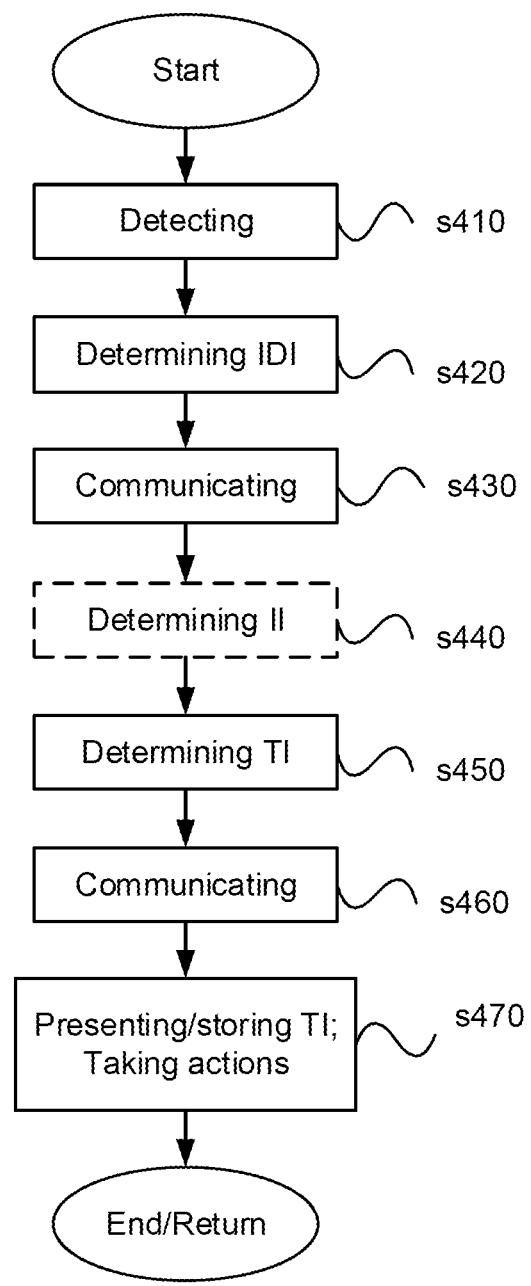
FIG. 4 is a schematic flowchart of a method according to an embodiment of the present disclosure.

FIG. 4 is a schematic flowchart of a method according to an embodiment of the disclosure.

The method comprises a first method step s410. The first method step s410 comprises the step of detecting signals S109 generated by movements/muscle activity of a user of the communications system 100. The signals S109 may be electro potential signals and/or g-force signals. After the method step s410 a method step s420 is performed.

The method step s420 comprises the step of determining Internal Digital Information IDI based upon the detected signals S109 by means of a first mapping function 1MF. This may be performed in the first electronic arrangement 101. The IDI is according to an example a number of data pairs (X,T). This is further depicted with reference to e.g. FIG. 3a. After the method step s420 a method step s430 is performed.

The method step s430 comprises the step of communicating the Internal Digital Information IDI from the first electronic arrangement 101 to the second electronic arrangement 102. This is according to one embodiment performed wirelessly. After the method step s430 a method step s440 is performed.

The method step s440 comprises the step of determining Intermediate Information II based upon the determined Internal Digital Information IDI. This may be performed in the second electronic arrangement 102. This step is optional. According to this step, IDI is converted to II expressed in Morse code. After the method step s440 a method step s450 is performed.

The method step s450 comprises the step of determining Textual Information TI on the basis of the IDI (determined according to s430) and/or on the basis of II (determined according to s440). This is performed by means of a second mapping function 2MF. This may be performed in the second electronic arrangement 102. The textual information may comprise alphanumerical characters, or any relevant characters, symbols and/or signs. After the method step s450 a method step s460 is performed.

The method step s460 comprises the step of communicating the TI from the second electronic arrangement 102 to the third electronic arrangement 103. This is according to one embodiment performed wirelessly. After the method step s460 a method step s470 is performed.

The method step s470 comprises the step of presenting the TI by means of the third electronic arrangement 103. According to one example the TI is presented/displayed by means of a screen or monitor being a part of the third electronic arrangement 103. The step s470 may also comprise the step of storing the TI in a memory of the third arrangement 103.

According to one example, the step s470 comprises the step of taking actions. A user of the third electronic arrangement may take actions based upon the content of the TI. One example of such actions may be to respond to the user of the first/second electronic arrangement 101/102. Another example of such actions may be to forward at least parts of the received TI to a third party. One example of such actions may be to alert emergency/rescue services. After the method step s470 is method is ended or returned.

Figure 5:
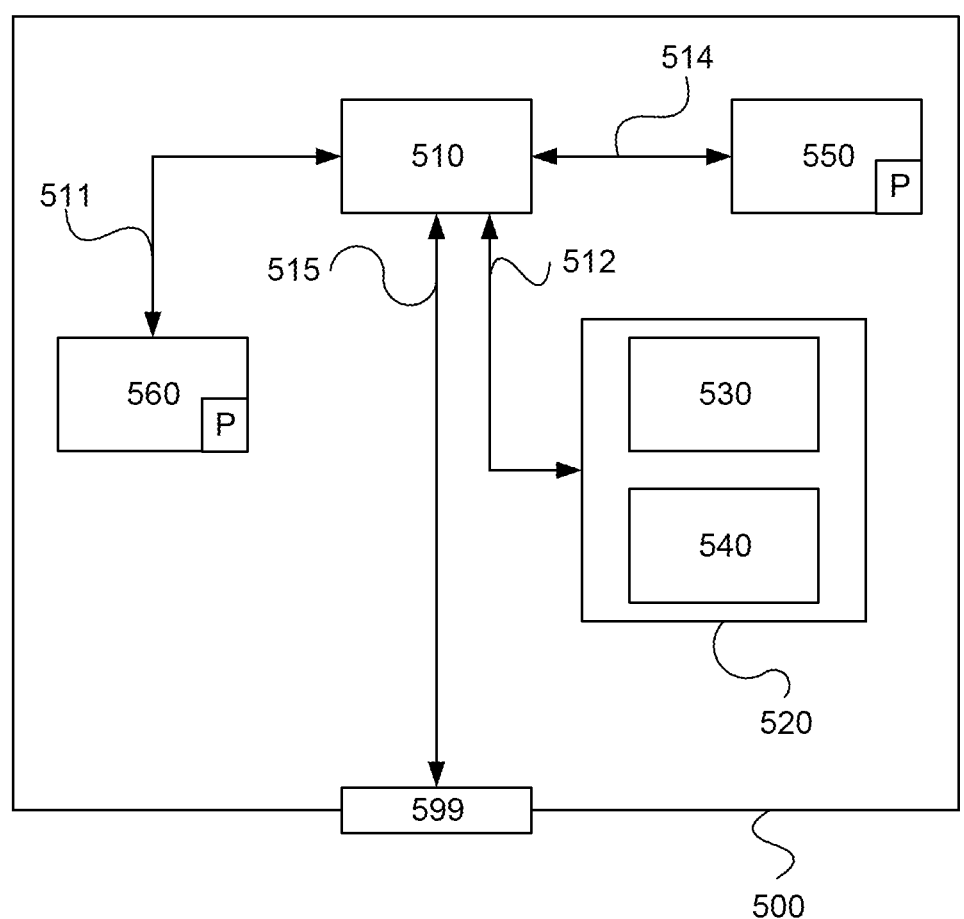
FIG. 5 schematically illustrates a computer according to an embodiment of the present disclosure.

FIG. 5 is a diagram of one version of a device 500. The electronic arrangements 101, 102 and 103 described with reference to FIGS. 1 and 2 may in one version comprise the device 500. The device 500 comprises a non-volatile memory 520, a data processing unit 510 and a read/write memory 550. The non-volatile memory 520 has a first memory element 530 in which a computer program, e.g. an operating system, is stored for controlling the function of the device 500. The device 500 further comprises a bus controller, a serial communication port, I/O means, an A/D converter, a time and date input and transfer unit, an event counter and an interruption controller (not depicted). The non-volatile memory 520 has also a second memory element 540.

According to an example embodiment there is provided a computer program comprising routines for communicating information from the wearable sensor configuration 110 comprising the sensor unit 115 and the first electronic arrangement 101, wherein the wearable sensor configuration 110 is arranged to operate in the communications system 100.

The computer program P may comprise routines for controlling detection of signals S109 generated by movements/muscle activity of a user of the communications system 100, 100'. The computer program P may comprise routines for determining Internal Digital Information IDI based upon the detected signals S109 by means of a first mapping function 1MF.

The computer program P may comprise routines for controlling communication of the Internal Digital Information IDI from the first electronic arrangement 101 to the second electronic arrangement 102.

The computer program P may comprise routines for determining Intermediate Information II based upon the determined Internal Digital Information IDI.

The computer program P may comprise routines for controlling communication of the TI from the second electronic arrangement 102 to the third electronic arrangement 103

The computer program P may comprise routines for controlling presentation of the TI by means of the third electronic arrangement 103. The TI may be presented visually/audibly/tactile to a user of the third electronic arrangement 103.

The computer program P may comprise routines for performing any one of the method steps and hardware functions detailed with reference to the disclosure.

The program P may be stored in an executable form or in compressed form in a memory 560 and/or in a read/write memory 550.

Where it is stated that the data processing unit 510 performs a certain function, it means that it conducts a certain part of the program that is stored in the memory 560 or a certain part of the program that is stored in the read/write memory 550.

The data processing device 510 can communicate with a data port 599 via a data bus 515.

The non-volatile memory 520 is intended for communication with the data processing unit 510 via a data bus 512. The separate memory 560 is intended to communicate with the data processing unit via a data bus 511. The read/write memory 550 is arranged to communicate with the data processing unit 510 via a data bus 514. The links L110, L115 and L150, for example, may be connected to the data port 599 (see FIGS. 1, 2 and 5).

When data are received on the data port 599, they are stored in the second memory element 540. When input data received have been stored, the data processing unit 510 will be prepared to conduct code execution as described above.

Parts of the methods herein described may be conducted by the device 500 by means of the data processing unit 510, which runs the program stored in the memory 560 or the read/write memory 550. When the device 500 runs the program, method steps and process steps herein described are executed.

The relevant method steps depicted herein may be performed by means of e.g. the device 500. Any suitable processing circuitry may be used for performing the disclosed method steps and hardware functions. The processing circuitry may be arranged in the first electronic arrangement 101, second electronic arrangement 102 and/or the third electronic arrangement 103.

The computer program product comprises a computer readable medium such as, for example a universal serial bus (USB) memory, a plug-in card, an embedded drive or a read only memory (ROM). The computer readable medium has stored thereon a computer program comprising program instructions. The computer program is loadable into the processing circuitry comprised in any of the first electronic arrangement 101, second electronic arrangement 102 and/or the third electronic arrangement 103. When loaded into the processing circuitry, the computer program may be stored in a memory associated with or comprised in the processing circuitry and executed by a processor. According to some embodiments, the computer program may, when loaded into and run by the processing circuitry, cause execution of method steps according to, for example, the method steps illustrated in FIG. 4 or otherwise described herein.

According to one example there is provided a computer program product comprising instructions which, when the program is executed by a computer, e.g. the first electronic arrangement 101, the second electronic arrangement 102 and the third electronic arrangement 103, cause the computer to carry out any one of the method steps of the present disclosure.

According to one example there is provided a computer-readable storage medium comprising instructions which, when executed by a computer, e.g. the first electronic arrangement 101, the second electronic arrangement 102 and the third electronic arrangement 103, cause the computer to carry out any one of the method steps of the present disclosure.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, apparatus, modules, systems, and computer program products. It should be appreciated that the example embodiments presented herein may be practiced in any combination with each other.

In the drawings and specification, there have been disclosed exemplary embodiments. However, many variations and modifications can be made to these embodiments.

Accordingly, although specific terms are employed, they are used in a generic and descriptive sense only and not for purposes of limitation, the scope of the embodiments being defined by the following claims.

The invention claimed is:

1. A method for communicating information from a wearable sensor configuration comprising a sensor unit, a first electronic arrangement, and a second electronic arrangement, wherein the wearable sensor configuration is arranged to operate in a communications system, the method comprising:
    detecting signals generated by muscle activity of a user of the communications system;
    determining Internal Digital Information on the basis of the detected signals by means of a first mapping function in the first electronic arrangement, wherein the Internal Digital Information comprises a set of number pairs, each number pair comprising a first number representing a certain muscle signal change, the signal change comprising one of "on" or "off", and a second number representing a timestamp relating to said detected muscle signal change;
    wherein when the first number representing the certain muscle signal change equals 1 and the second number representing the timestamp relating to said detected muscle signal change equals 103 ms, the number pair represents the start of a dot in Morse code,
    when the first number representing the certain muscle signal change equals 0 and the second number representing the timestamp relating to said detected muscle signal change has a value, the number pair represents the start of a gap within a character in Morse code,
    when the first number representing the certain muscle signal change equals 1 and the second number representing the timestamp relating to said detected muscle signal change equals 291 ms, the number pair represents the start of a dash in Morse code, and
    wherein a duration of the dot in Morse code equals 95 ms, 96 ms, 102 ms, or 103 ms, and a duration of the dash in Morse code equals 294 ms, 296 ms, or 327 ms;
    communicating the Internal Digital Information to a second electronic device from the wearable sensor configuration, wherein the second electronic arrangement converts the Internal Digital Information to Intermediate Information in Morse code;
    determining Textual Information based on the Intermediate Information, which is based on the Internal Digital Information by means of a second mapping function in the second electronic arrangement.

2. The method according to claim 1, further comprising the steps of:
    determining the Intermediate Information based on the Internal Digital Information; and
    determining the Textual Information based on the Internal Digital Information by means of the second mapping function.

3. The method according to claim 1, further comprising the steps of:
    setting-up the first mapping function by predetermined rules and/or by choice of a user; and/or
    setting-up the second mapping function by predetermined rules and/or by choice of a user.

4. A computer program product consisting of a non-transitory computer-readable storage medium comprising instructions which, when the program is executed by a computer, cause the computer to carry out the steps of the method according to claim 1.

5. A non-transitory computer-readable storage medium comprising instructions which, when executed by a computer, cause the computer to carry out the steps of the method according to claim 1.

* * * * *